(12) United States Patent
Joseph, Jr. et al.

(10) Patent No.: US 7,759,055 B2
(45) Date of Patent: Jul. 20, 2010

(54) COMPOSITIONS OF SOLUTION FOR SEQUENCING REACTION CLEAN-UP

(75) Inventors: Gabriels E. Joseph, Jr., Arlington, MA (US); Masaharu Mabuchi, Beverly, MA (US)

(73) Assignee: Millipore Corporation, Billera, MA (US)

( * ) Notice: Subject to any disclaimer, the term of this patent is extended or adjusted under 35 U.S.C. 154(b) by 281 days.

(21) Appl. No.: 10/524,609

(22) PCT Filed: Aug. 25, 2003

(86) PCT No.: PCT/US03/26557
§ 371 (c)(1),
(2), (4) Date: Feb. 14, 2005

(87) PCT Pub. No.: WO2004/020673
PCT Pub. Date: Mar. 11, 2004

(65) Prior Publication Data
US 2006/0166200 A1    Jul. 27, 2006

Related U.S. Application Data

(60) Provisional application No. 60/406,654, filed on Aug. 28, 2002.

(51) Int. Cl.
C12Q 1/68 (2006.01)
C07C 277/00 (2006.01)
C07C 279/00 (2006.01)
C07H 21/02 (2006.01)

(52) U.S. Cl. .................. 435/6; 536/23.1; 564/241
(58) Field of Classification Search .......... 435/6; 564/241; 536/23.1
See application file for complete search history.

(56) References Cited

U.S. PATENT DOCUMENTS

| 5,202,456 | A | * | 4/1993 | Rando ................. 558/438 |
| 5,292,869 | A | | 3/1994 | Schryvers |
| 5,958,727 | A | * | 9/1999 | Brody et al. ......... 435/69.1 |
| 6,114,388 | A | | 9/2000 | Geffard |
| 6,165,770 | A | | 12/2000 | Sjoholm et al. |
| 6,288,123 | B1 | | 9/2001 | Katragadda et al. |
| 2002/0098192 | A1 | | 7/2002 | Lee et al. |

FOREIGN PATENT DOCUMENTS

| WO | WO 86/04583 A | 8/1986 |
| WO | WO 99/22021 A | 5/1999 |
| WO | WO 01/09389 A | 2/2001 |
| WO | WO 01/19482 A | 3/2001 |
| WO | WO 02/44414 A | 6/2002 |
| WO | WO 03/058196 A | 7/2003 |

OTHER PUBLICATIONS

Vogelstein, B., et al. "Preparataive and Analytical Purfication of DNA From Agarose" Proc. of the National Academy of Sciences of the USA, vol. 76, No. 2, (Feb. 1, 1979) pp. 615-619.
International Search Report dated Dec. 16, 2003.

* cited by examiner

*Primary Examiner*—Sue Liu (57) ABSTRACT

Wash solution and method for purifying sequencing reaction product. The wash solution comprises an effective amount of guanidine in a low ionic solution to reduce or eliminate the presence of dye terminators in a sequencing reaction product. In its method aspects, the present invention comprises the addition of the wash solution to the sequencing reaction product prior to filtration, followed by filtration to reduce or eliminate unincorporated dye terminators. The purified sequencing products can then be resuspended and transferred to an appropriate substrate for sequencing or further preparation. Dye blobs formed from unincorporated dye terminators no longer interfere with the electropherograms generated upon electrophoresis of the sample.

29 Claims, 12 Drawing Sheets

COMPOSITIONS OF SOLUTION FOR SEQUENCING REACTION CLEAN-UP

CROSS REFERENCE TO RELATED APPLICATIONS

This application is the U.S. National Application of International Application No. PCT/US2003/026557, filed on Aug. 25, 2003, which claims the benefit of U.S. Provisional Application No. 60/406,654, filed on Aug. 28, 2002.

BACKGROUND

Commercially available DNA sequencing kits, such as the ABI PRISM® BigDye® Terminator v.1.0, 1.1, 2.0, 3.0 and 3.1 Ready Reaction Cycle Sequencing Kits available from Applied Biosystems, Inc. utilize fluorescently-labeled molecules or dye terminators as a component. For example, the dye terminators, deoxynucleoside triphosphates, sequencing enzyme, magnesium chloride and buffer are premixed and are suitable for performing fluorescence-based cycle sequencing reactions on single-stranded or double-stranded DNA templates and on polymerase chain reaction fragments.

Because dye terminators are not natural substrates of DNA polymerase, high concentrations generally must be provided relative to the natural dNTP substrates to ensure their incorporation into the polymerizing sequencing products. The unincorporated fluorescently-labeled molecules, however, are difficult to remove if present in high concentration. If they are not adequately removed, the unincorporated fluorescently-labeled molecules can interfere with downstream analysis (e.g., DNA sequencing), such as by co-migrating with short sequencing products during electrophoresis. Indeed, these molecules have a tendency to form insoluble complexes at high concentrations. They are particularly problematic in reactions that utilize high concentrations of sequencing chemistries (e.g., 1×, ½× and ¼× strength reactions).

Conventional methods for removing unincorporated dye terminators from sequencing reactions prior to electrophoresis involve alcohol precipitation and gel filtration. However, salts compete with sequencing products for electrokinetic injection onto capillary sequencing instruments and also must be removed. Ethanol precipitation has poor salt removal capabilities which detracts from its utility as a method for preparing samples prior to capillary electrophoresis because the efficiency of electrokinetic injection of sequencing products is inversely proportional to the salt concentration. Gel filtration is a centrifuge-based method which is difficult to automate, which is important for high throughput DNA sequencing.

Another method of removing unincorporated fluorescently-labeled molecules such as dye terminators involves using MultiScreen® or Montage™ 384-SEQ ultrafiltration plates commercially available from Millipore Corporation. These plates are fully automatable and provide a cost-and-time efficient alternative to conventional ethanol precipitation for dye-terminator removal. They operate by vacuum filtration, thereby eliminating the need for centrifugation, ethanol drying steps and manifold disassembly routines. Solvents such as formamide or EDTA aid in the solubilization of dye terminators and prevention of aggregate formation. The sequencing products are purified by filtering to dryness and then washing salts an dye terminators to waste. The purified sequencing products are then resuspended from the membrane surface and are ready for introduction into a DNA sequencer.

However, the introduction of new sequencing chemistries by various manufacturers continues to present purification challenges. In addition, although current ultrafiltration technology provides substantially purified DNA sequencing products at reaction strengths of one microliter of sequencing reagent per DNA sequencing reaction (⅛$^{th}$ BDT v3.0), at higher concentrations artifacts known as dye blobs become apparent on electropherograms. These artifacts are also commonly visible using other clean-up methods such as gel filtration and alcohol precipitation despite specific modifications to the protocol recommended by the manufacturer to eliminate them.

It therefore would be desirable to provide a cost-effective and efficient solution for reducing or eliminating unincorporated fluorescently-labeled molecules and residual salts from sequencing reactions.

SUMMARY

The problems of the prior art have been overcome by the present invention, which provides a wash solution and method for purifying sequencing reaction product. The wash solution preferably comprises between about 1 mM to about 60 mM of guanidine in a low ionic solution. In its method aspects, the present invention comprises the addition of the wash solution to the sequencing reaction product prior to filtration, followed by filtration to reduce or eliminate unincorporated dye terminators. The purified sequencing products can then be resuspended and transferred to an appropriate substrate for sequencing or further preparation. Dye blobs formed from unincorporated dye terminators no longer interfere with the resolution of electropherograms generated upon electrophoresis of the sample.

DETAILED DESCRIPTION

The present inventors have found that effective amounts of guanidine in the sequencing reaction product disrupt aggregates and/or prevent their formation, as evidenced by electropherograms even at higher reaction scales. Effective amounts of guanidine are amounts sufficient to reduce the presence of unincorporated dye terminators to an extent where they do not deleteriously interfere with downstream analysis, particularly the electrophoresis of the sequencing reaction products. Deleterious interference with electrophoresis is manifested in the appearance of dye blobs in electropherograms, wherein the presence of the dye blobs make it difficult or impossible to accurately resolve the sequencing products. Such interference is particularly noticeable with shorter DNA. Higher concentrations of dye terminators also interfere further downstream during sequencing.

Excessive amounts of guanidine can result in the unacceptable loss of shorter sequencing product. Insufficient amounts of guanidine can result in inadequate reduction of deleterious artifacts, or the reappearance thereof. Suitable amounts of guanidine range from about 1 to about 60 mM, more preferably from about 1 to about 30 mM, with about 5 to about 10 mM being particularly preferred. It is surprising that only relatively low concentrations of guanidine were effective in sufficiently reducing or eliminating dye blobs from the electropherograms.

Preferably the guanidine is used in the form of its salt. Suitable salts include chaotropes of guanidine, such as guanidine carbonate or guanidine hydrochloride. The particular salt used should be chosen to avoid undesirable interactions in the reaction. Preferably the guanidine salt is used in a low ionic solution, such as 0.3 mM EDTA of pH from about 5-11, preferably 8-10.

In its method aspects, the present invention comprises the steps of providing a defined quantity of sequencing reaction product, providing at least one ultrafiltration membrane having at least one surface, introducing the sequencing reaction product onto the surface of the ultrafiltration membrane, adding the guanidine wash solution either prior to or after the sequencing reaction product is introduced onto the ultrafiltration membrane surface, applying a driving force, such as constant pressure differential or vacuum, to the surface of the membrane sufficient to produce the sequencing reaction product substantially free of contaminants. The addition of the guanidine wash solution and application of a driving force may be repeated. The sequencing reaction product is retained on the membrane surface while contaminants, including dye terminators, are filtered to waste. Preferably the sequencing reaction product is filtered to dryness (e.g., no visible fluid remains), and the driving force is maintained for about 15 seconds after filtration to dryness (where multiple filtrations are carried out simultaneously in a multiwell device, preferably the driving force is maintained until the last well is empty). The sequencing reaction product may be washed (such as with the wash solution of the present invention), filtered to dryness again, resuspended in a low ionic solution known to those skilled in the art, such as formamide or water, and transferred (e.g., by pipetting) to an appropriate substrate for sequencing (e.g., electrokinetic injection), restriction digestion or further preparation.

The following Table illustrates suitable amounts of components for various concentrations of sequencing chemistries using the ABI BigDye® Terminator kit:

| Component | Reaction Strength | | | | |
| --- | --- | --- | --- | --- | --- |
| | 1x | ½ x | ½ x | ¼ x | ¼ x |
| Template Plasmid (50 ng/μL) PCR (5 fmol/μL) | 2.0 μL | 2.0 μL | 2.0 μL | 2.0 μL | 2.0 μL |
| 2.5x buffer* | 0 μL | 4.0 μL | 0 μL | 2.0 μL | 0 μL |
| Primer (5 pmol/μL) | 1.0 μL | 1.0 μL | 1.0 μL | 1.0 μL | 1.0 μL |
| BDT Premix | 8.0 μL | 4.0 μL | 4.0 μL | 2.0 μL | 2.0 μL |
| Milli-Q ™ H$_2$O | 9.0 μL | 9.0 μL | 3.0 μL | 3.0 μL | 0 μL |
| Total | 20 μL | 20 μL | 10 μL | 10 μL | 5 μL |

*2.5x Buffer: 200 mM Tris-HCl, pH 9.0, 5 mM MgCl$_2$; BigDye mix, primer, 2.5x buffer and water can be mixed together to make sequencing "cocktail"; an appropriate volume of cocktail is then dispensed into each well.

Suitable ultrafiltration membranes have molecular cutoffs between about 1000 and 30,000 Daltons, preferably between about 3,000 and 15,000 Daltons. They may be made from a variety of materials, including but not limited to polyamides, polysulphones, polyethersulphones, polyarylsulphones, cellulosics, regenerated cellulose and polyvinylidene fluoride. They may be symmetrical or asymmetrical, with the latter being preferred. For high throughput applications, preferably a plurality of ultrafiltrations are carried out simultaneously, most preferably using a 384 well filter plate. Other size plates, including 96 well format, also can be used. Suitable filter plates include the MultiScreen® or MONTAGE™ 384-SEQ filter plates commercially available from Millipore Corporation.

Suitable vacuum is that sufficient to reduce or remove the dye terminators, and generally ranges from about 15 to about 28 inches of mercury, preferably from about 23-25 inches of mercury. Generally the driving force is applied slightly (about 15 seconds) longer than the time necessary to remove all visible liquid from the wells, which typically is about 3-4 minutes.

EXAMPLE 1

Figure 1A:
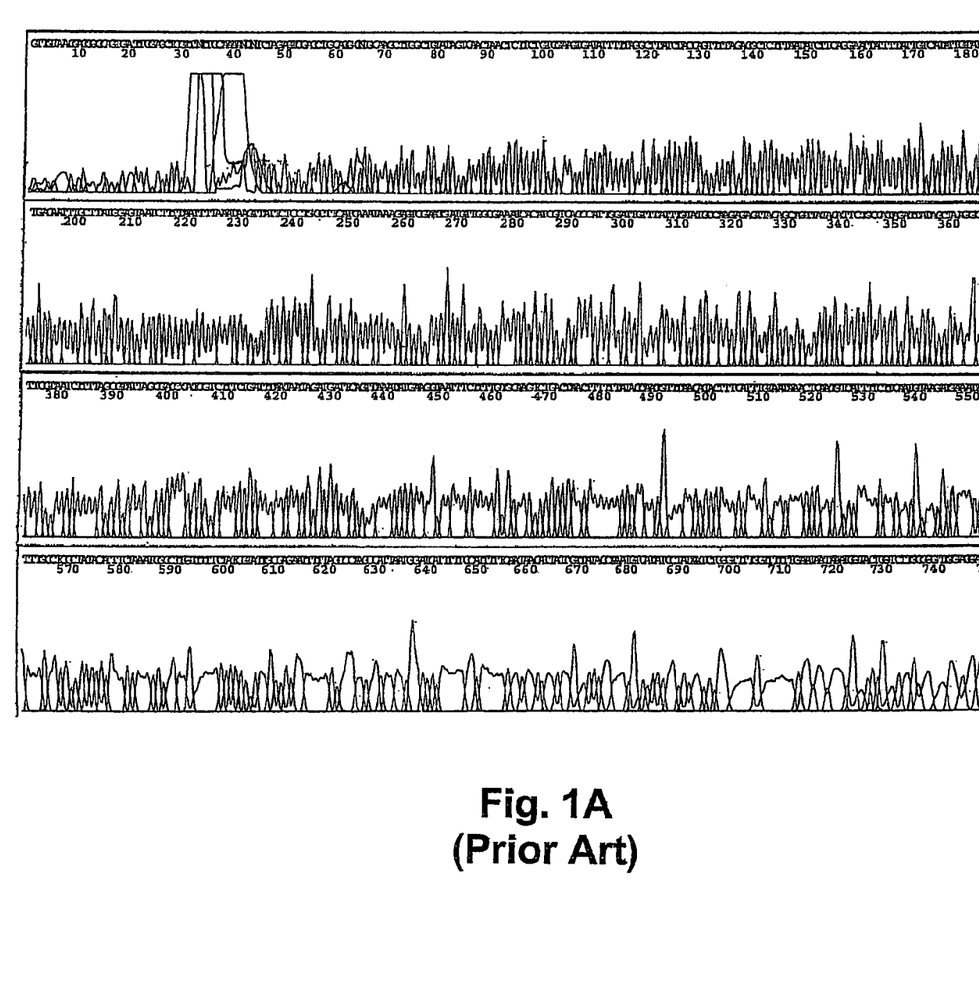
FIG. 1A is an electropherogram of a full scale reaction in accordance with the prior art.
Figure 1B:
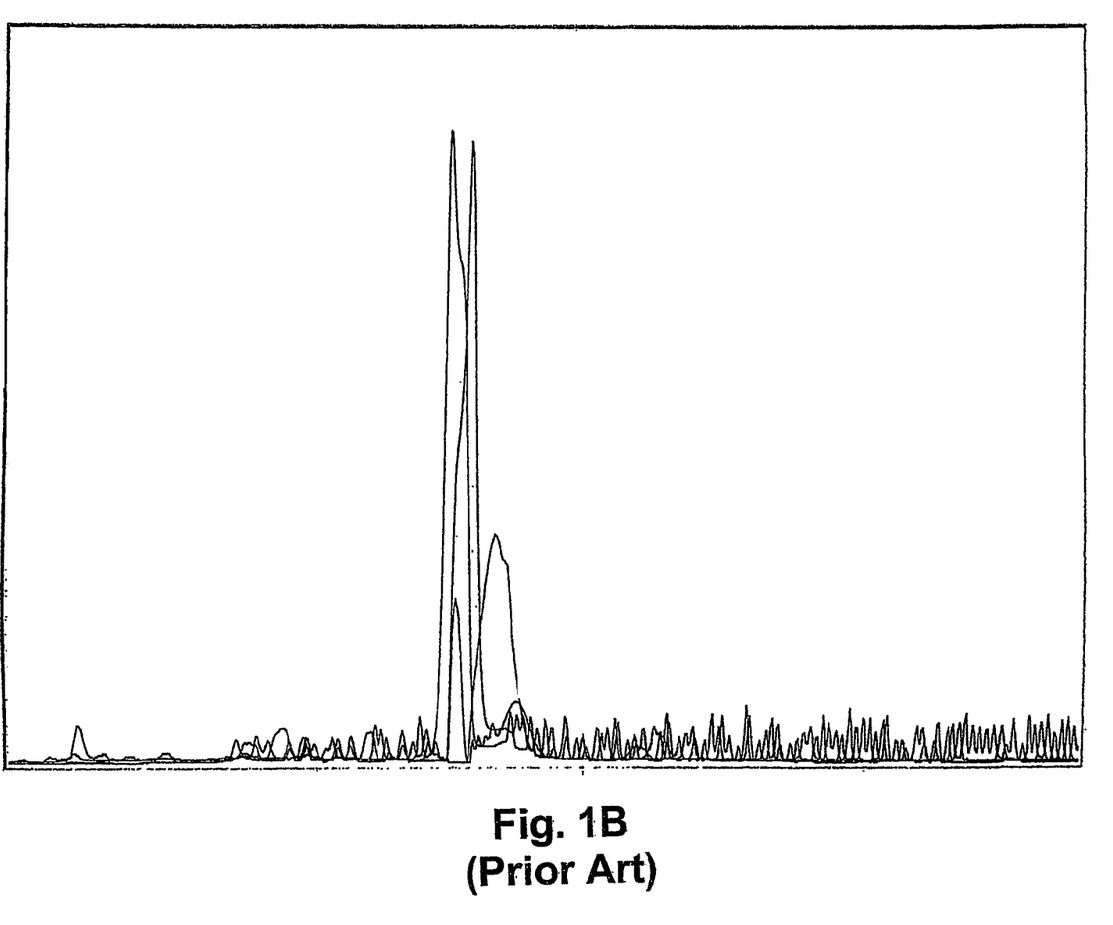
FIG. 1B is a raw trace of the reaction dye blobs of FIG. 1A.

A sequencing reaction was set up in a thermal cycling plate (96 wells) and amplified using an appropriate thermal cycling program. The reaction components were 5 pmol of M13 primer, 200 ng of pLH2 (template), 8 μl of BigDye pre-mix, and sufficient Milli-Q® water to bring the final volume to 20 μl. All of the mixture was transferred to a Montáge SEQ$_{96}$ plate commercially available from Millipore Corporation. The plate was placed on a vacuum manifold and vacuum of 23-25 inches Hg was applied for 3-4 minutes until no visible fluid remained in the wells. Vacuum was continued for about 15 seconds, and the plate was removed from the manifold. Excess fluid was removed from the bottom of the plate by pressing the plate briefly to a stack of paper towels. The plate was returned to the manifold, and 25 μl of was solution (no guanidine) was added. Vacuum was again applied at 23-25 inches Hg for 3-4 minutes until no visible fluid remained in the wells, and for about 15 seconds thereafter. The plate was removed from the manifold and excess fluid again was removed from the bottom of the plate by pressing the plate against a stack of paper towels. 25 μl of injection solution was added, and the DNA was resuspended by pipetting up and down 15-20 times. The purified sequencing products were injected into an ABI 3700 sequencer at 2 KV, 15 seconds. The result is shown in FIGS. 1A and 1B. Large dye blobs are apparent.

EXAMPLE 2

Figure 2A:
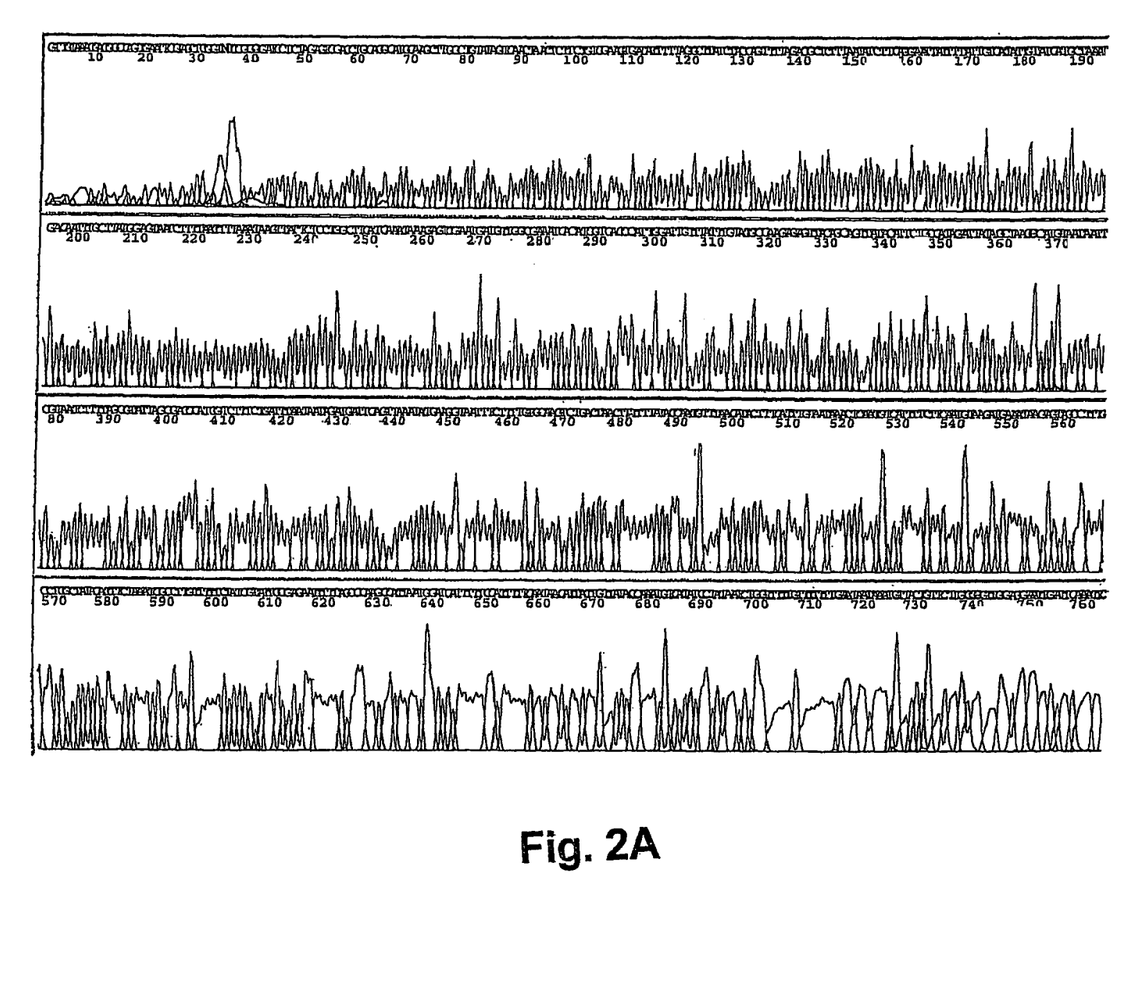
FIG. 2A is an electropherogram of a full scale reaction in accordance with the present invention.
Figure 2B:
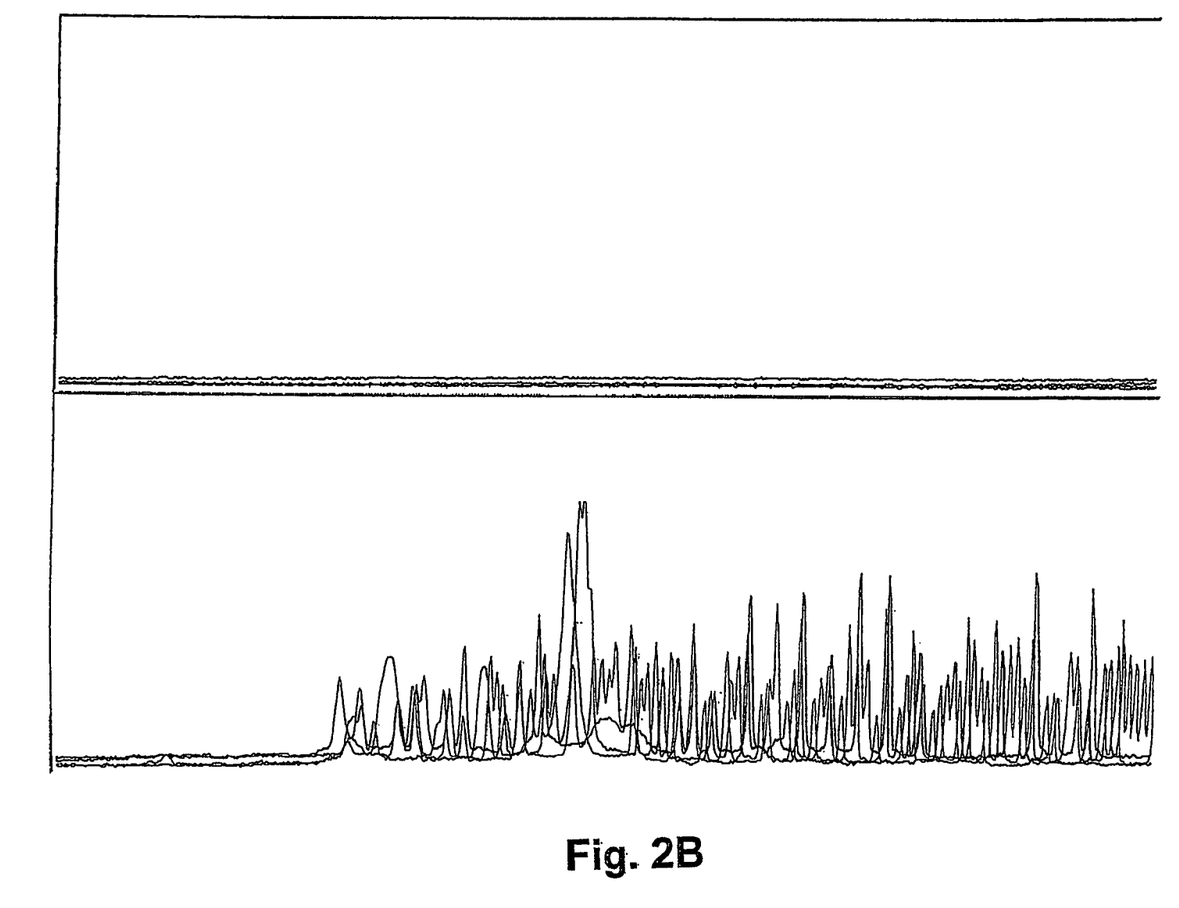
FIG. 2B is a raw trace of the reduced dye blobs of FIG. 2A.

A sequencing reaction was set up in a thermal cycling plate (96 wells) and amplified using an appropriate thermal cycling program. The reaction components were 5 pmol of M13 primer, 200 ng of pLH2 (template), 8 μl of BigDye pre-mix, and sufficient Milli-Q® water to bring the final volume to 20 μl. 30 μl of wash solution (no guanidine) was added to each sequencing reaction. After thermal cycling, 30 μl of sequencing wash solution comprising 0.5 mM guanidine in 0.3 mM EDTA of pH 8 was added to each of the reactions and mixed gently. All of the mixture was transferred to a Montáge SEQ$_{96}$ plate commercially available from Millipore Corporation. The plate was placed on a vacuum manifold and vacuum of 23-25 inches Hg was applied for 3-4 minutes until no visible fluid remained in the wells. Vacuum was continued for about 15 seconds, and the plate was removed from the manifold.

Excess fluid was removed from the bottom of the plate by pressing the plate briefly to a stack of paper towels. The plate was returned to the manifold, and 25 µl of the sequencing wash solution was added. Vacuum was again applied at 23-25 inches Hg for 3-4 minutes until no visible fluid remained in the wells, and for about 15 seconds thereafter. The plate was removed from the manifold and excess fluid again was removed from the bottom of the plate by pressing the plate against a stack of paper towels. 25 µl of injection solution was added, and the DNA was resuspended by pipetting up and down 15-20 times. The purified sequencing products were injected into an ABI 3700 sequencer at 2 kV, 15 seconds. The result is shown in FIGS. 2A and 2B. The reduction in dye blobs compared to FIGS. 1A and 1B is apparent.

EXAMPLE 3

Figure 3A:
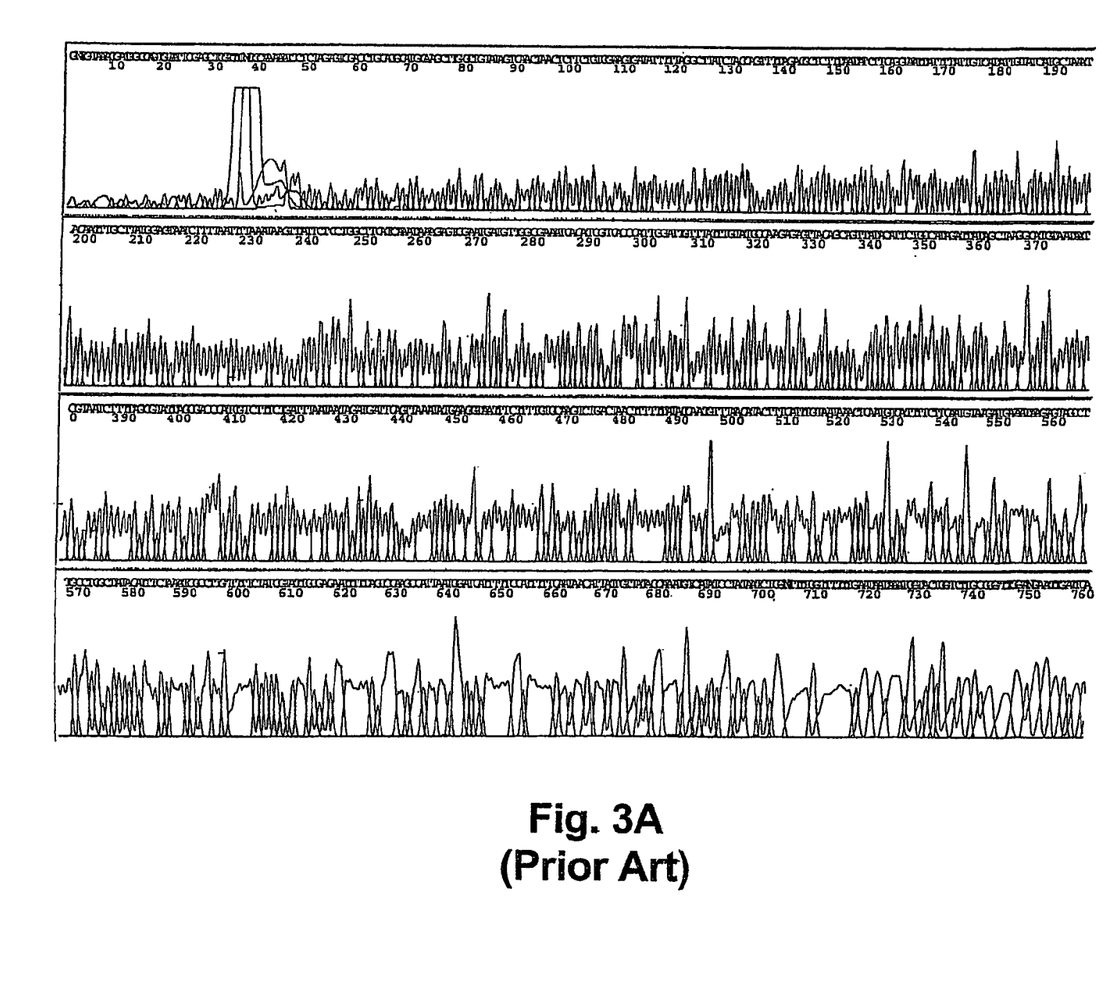
FIG. 3A is an electropherogram of a half scale reaction in accordance with the prior art.
Figure 3B:
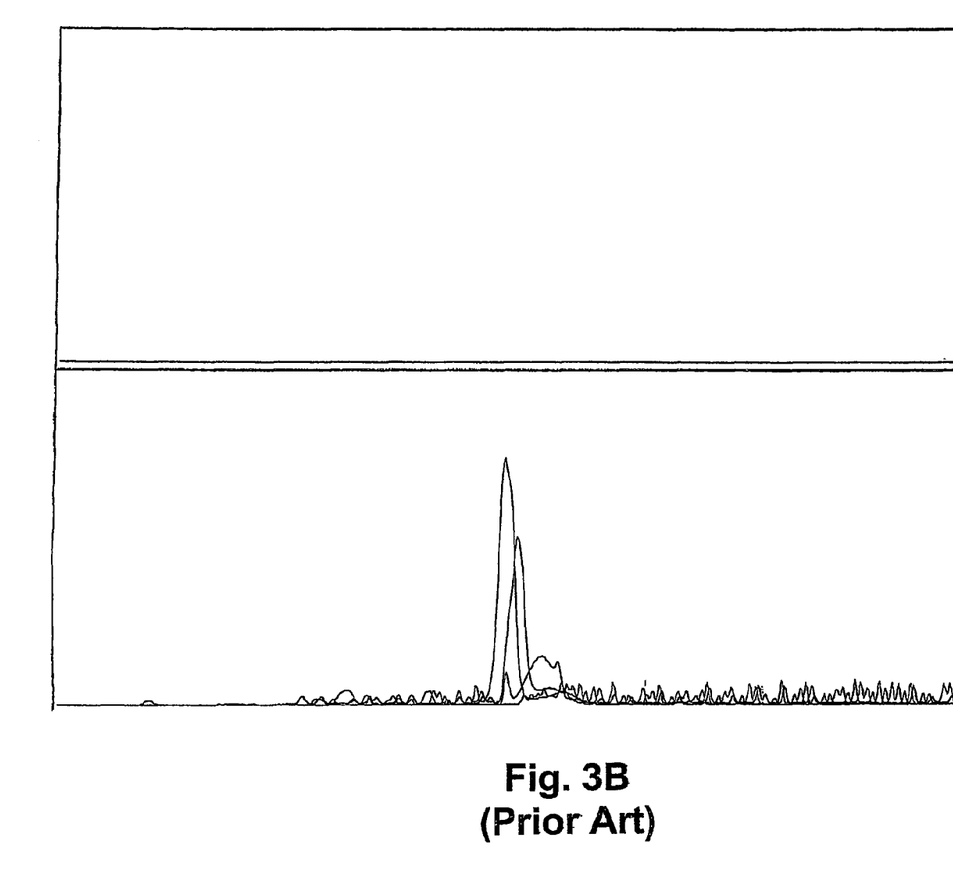
FIG. 3B is raw trace of the reaction dye blobs of FIG. 3A.

The same procedure as in Example 1 was carried out except at half reaction scale, wherein only 4 µl of BigDye pre-mix was used, and the final volume was 10 µl. The results are shown in FIGS. 3A and 3B.

EXAMPLE 4

Figure 4A:
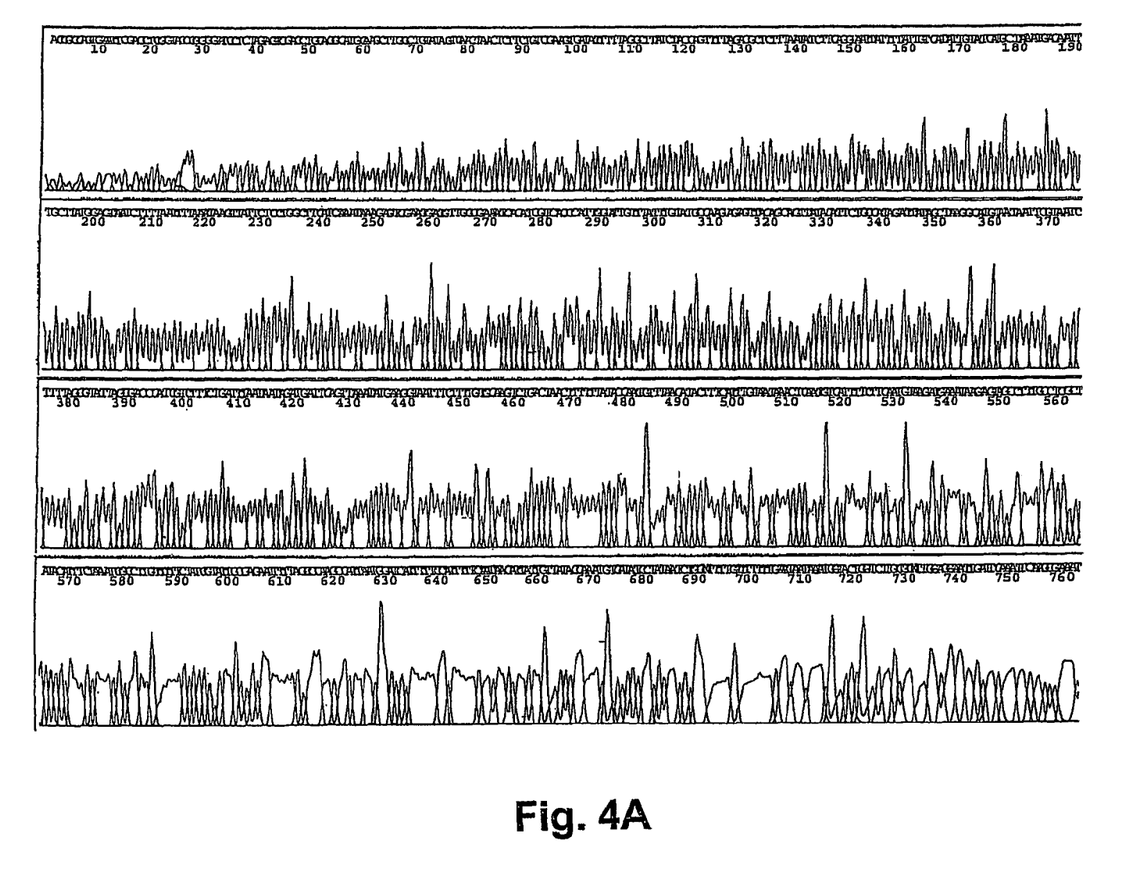
FIG. 4A is an electropherogram of a half scale reaction in accordance with the present invention.
Figure 4B:
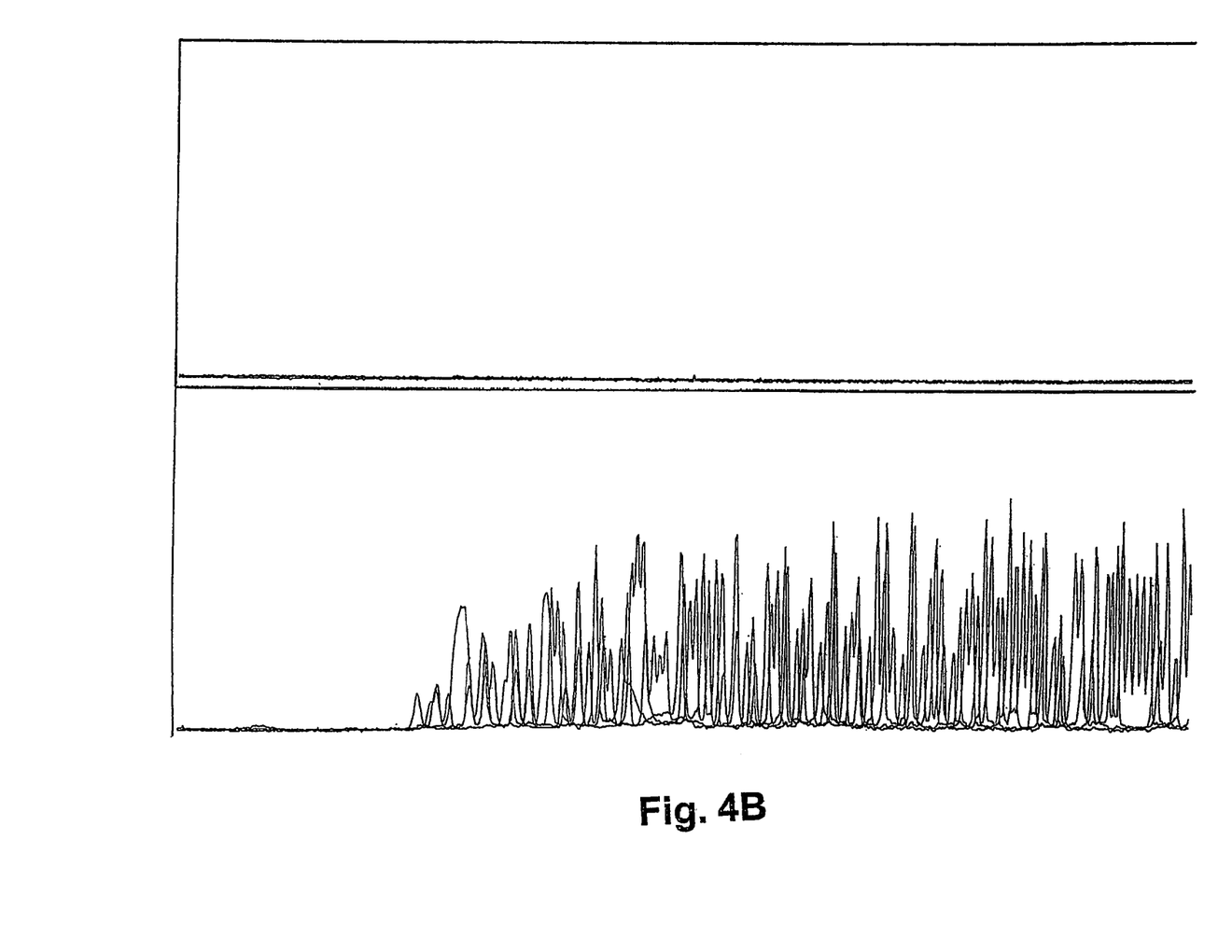
FIG. 4B is a raw trace showing the absence of dye blobs of FIG. 4A.

The same procedure as in Example 2 was carried out except at half reaction scale, wherein only 4 µl of BigDye pre-mix was used, and the final volume was 10 µl. The results are shown in FIGS. 4A and 4B. The absence of dye blobs is apparent in comparison to FIGS. 3A and 3B.

EXAMPLE 5

Figure 5A:
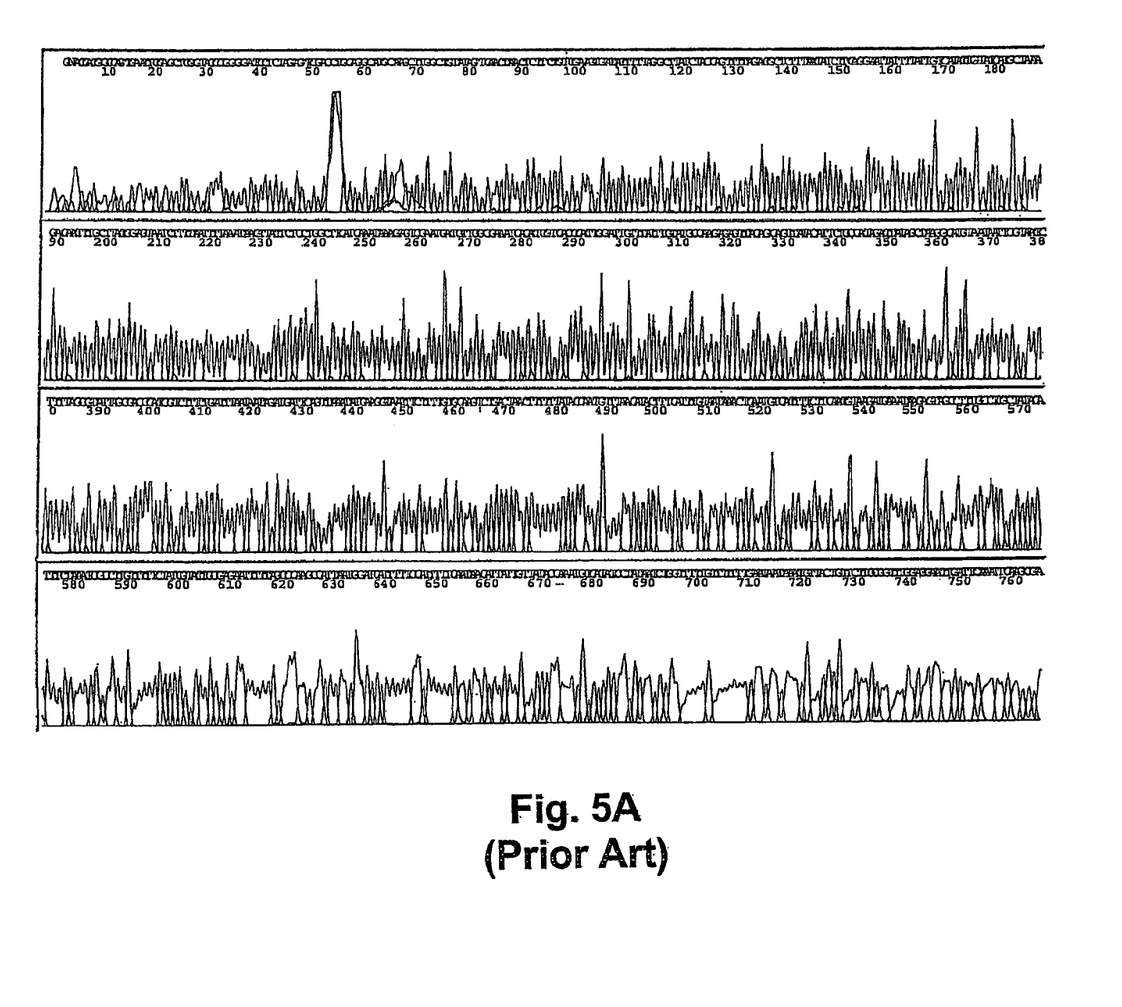
FIG. 5A is an electropherogram of a quarter scale reaction in accordance with the prior art.
Figure 5B:
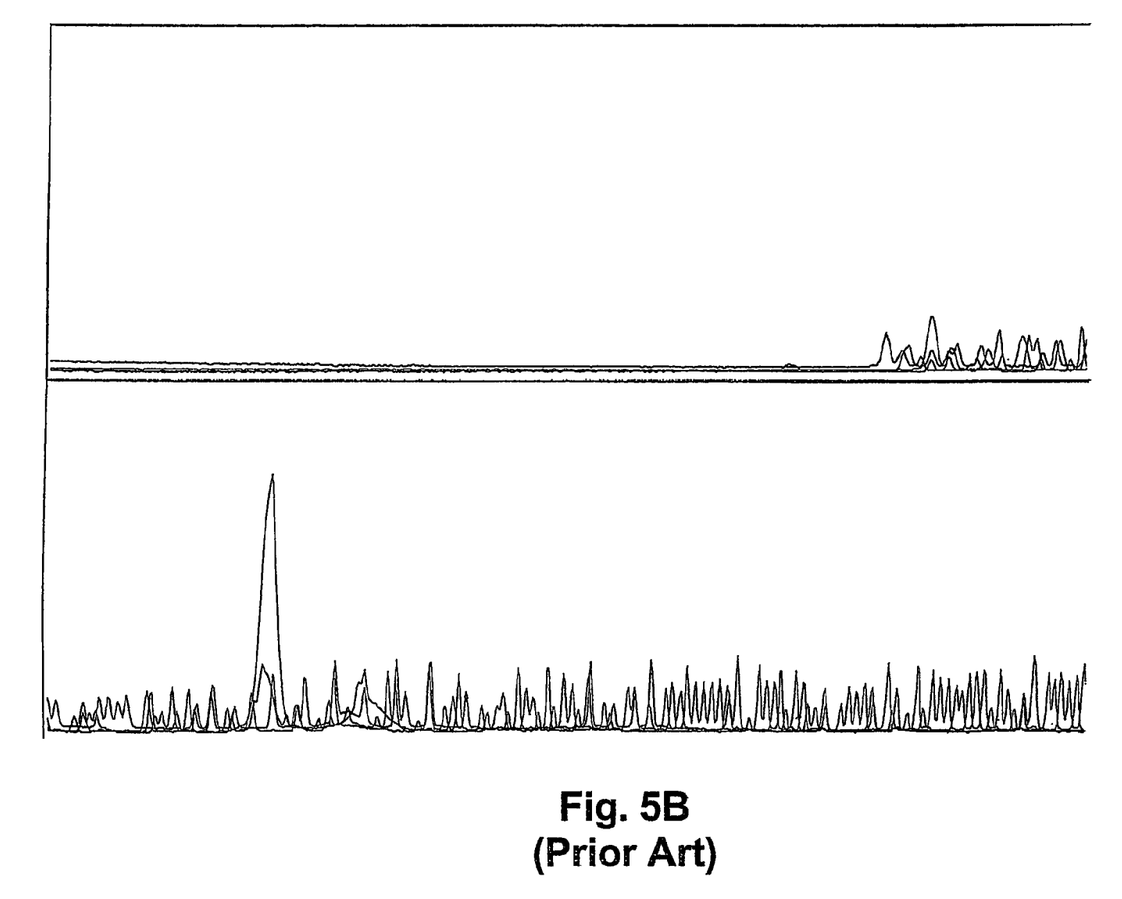
FIG. 5B is raw trace showing the reaction dye blobs in FIG. 5A.

The same procedure as in Example 1 was carried out except at quarter reaction scale, wherein only 2 µl of BigDye pre-mix was used, and the final volume was 5 µl. The injection into an ABI 3100 Avant sequencer was at 1 kV, 22 seconds. The results are shown in FIGS. 5A and 5B.

EXAMPLE 6

Figure 6A:
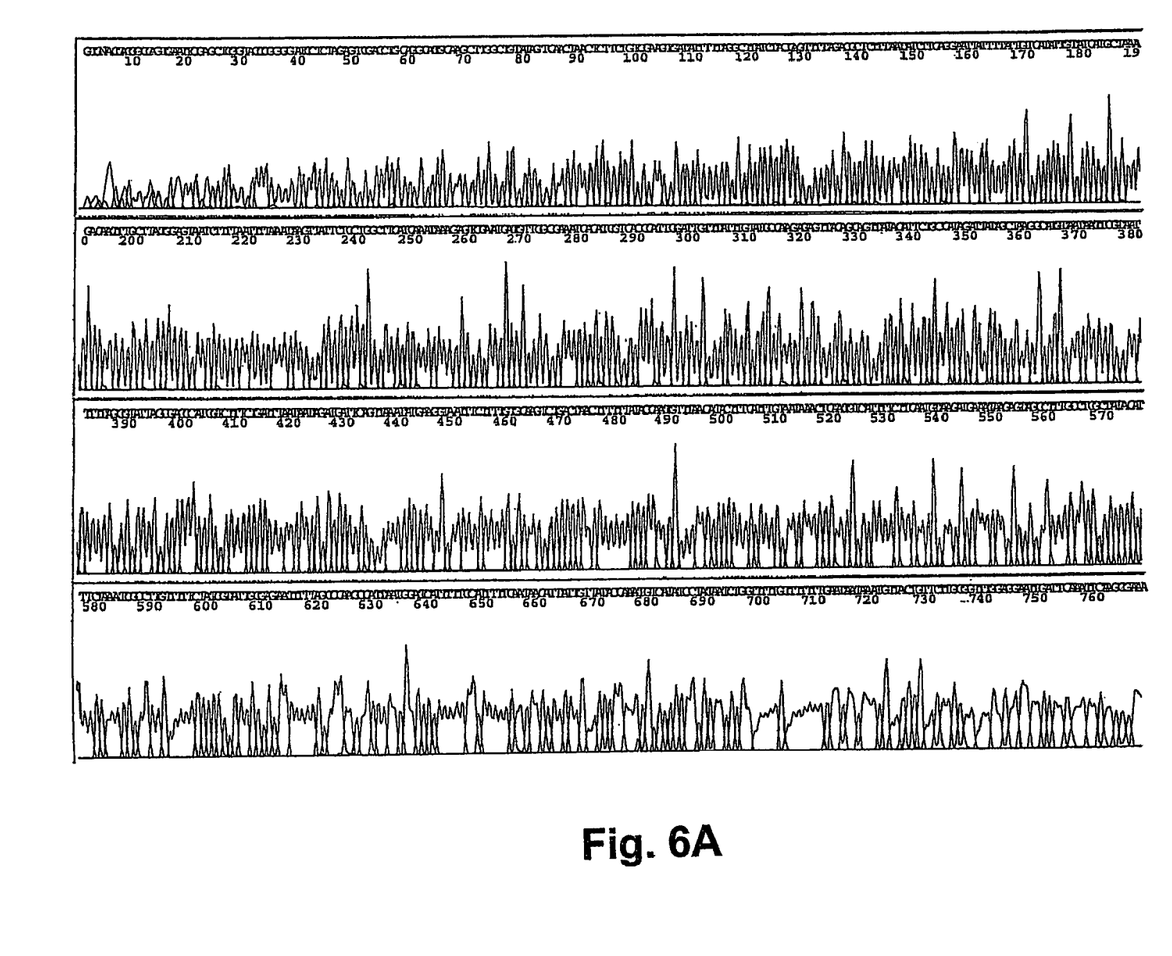
FIG. 6A is an electropherogram of a quarter scale reaction in accordance with the present invention.
Figure 6B:
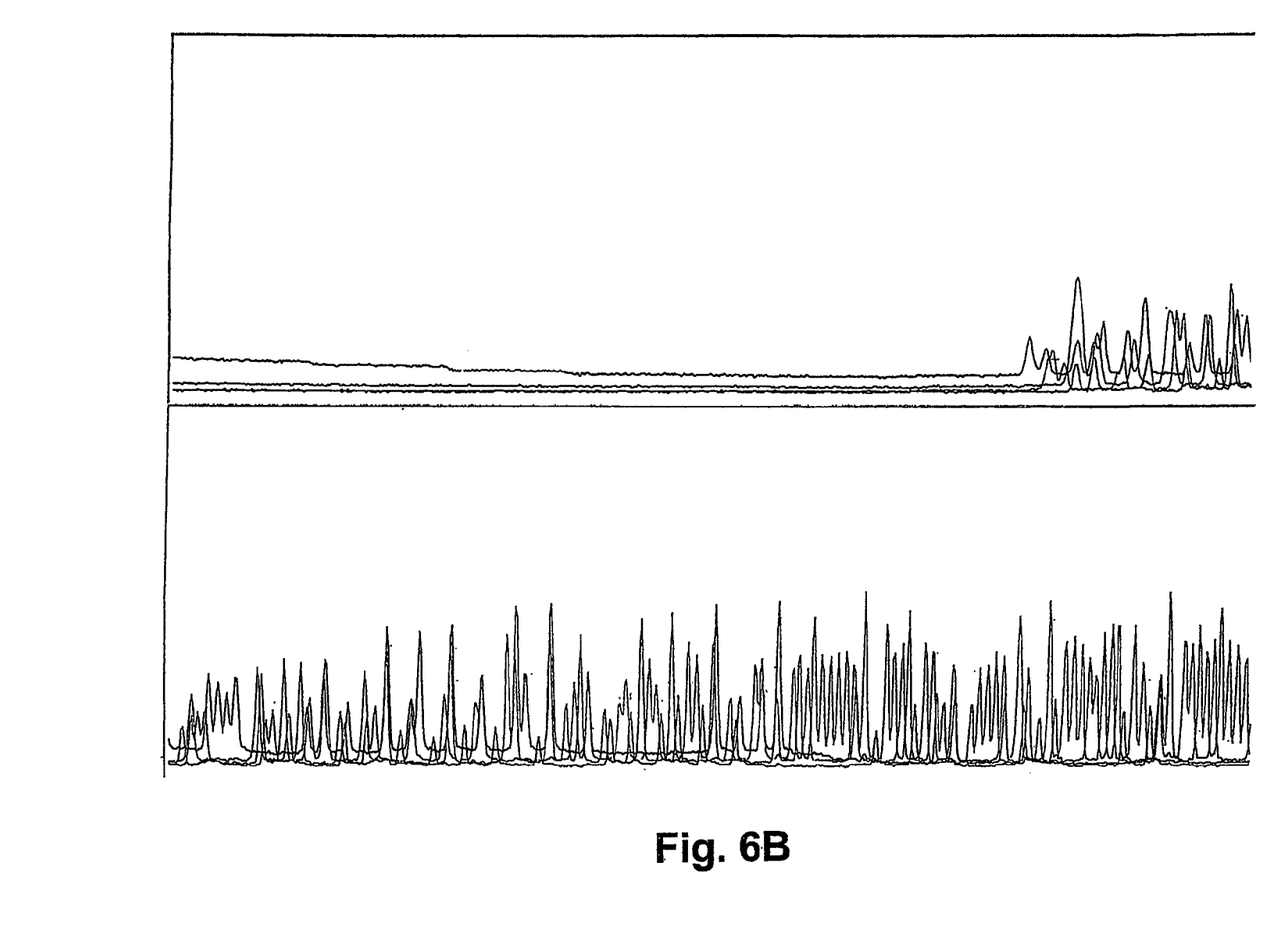
FIG. 6B is a raw trace showing the absence of dye blobs of FIG. 6A.

The same procedure as in Example 2 was carried out except at half reaction scale, wherein only 2 µl of BigDye pre-mix was used, and the final volume was 5 µl. The injection into an ABI 3100 Avant sequencer was at 1 kV, 22 seconds. The results are shown in FIGS. 6A and 6B. The absence of dye blobs is apparent in comparison to FIGS. 5A and 5B.

The invention claimed is:

1. A method for purifying sequencing reaction product by removing unincorporated dye terminators from a sequencing reaction, comprising:
   a) providing sequencing reaction product having unincorporated dye terminators;
   b) providing at least one ultrafiltration membrane having at least one surface;
   c) providing a solution comprising an amount of guanidine less than 5 mM effective for removing the unincorporated dye terminators from said sequencing reaction;
   d) introducing said sequencing reaction product and said solution to said at least one surface of said ultrafiltration membrane; and
   e) applying a driving force to said ultrafiltration membrane to produce purified sequencing reaction product by removing unincorporated dye terminators from the sequencing reaction product.

2. The method of claim 1, further comprising resuspending said purified sequencing reaction product in a low ionic solution.

3. The method of claim 2, further comprising transferring said resuspended sequencing reaction product to a substrate for sequencing.

4. The method of claim 1, wherein said solution comprising said amount of guanidine further comprises EDTA.

5. The method of claim 1, wherein said amount of guanidine is from about 0.5 mM to less than 5 mM.

6. The method of claim 1, wherein said amount of guanidine is from about 0.5 mM to about 1 mM.

7. The method of claim 1, wherein in step (e) the driving force is maintained until the purified sequencing reaction product is filtered to dryness such that no visible fluid remains.

8. The method of claim 1, wherein in step (d) the guanidine solution is added onto the ultrafiltration membrane surface prior to the addition of the sequencing reaction product onto the ultrafiltration membrane surface.

9. The method of claim 1, wherein in step (d) the guanidine solution is added onto the ultrafiltration membrane surface after to the addition of the sequencing reaction product onto the ultrafiltration membrane surface.

10. The method of claim 2, wherein the low ionic solution is selected from the group consisting of water, formamide and mixtures thereof.

11. The method of claim 1, wherein in step (d) the ultrafiltration membrane has a molecular cutoff between about 1,000 and 30,000 Daltons.

12. The method of claim 1, wherein in step (d) the ultrafiltration membrane has a molecular cutoff between about 3,000 and 15,000 Daltons.

13. The method of claim 1, wherein in step (d) the ultrafiltration membrane comprises a material selected from the group consisting of polyamides, polysulphones, polyethersulphones, polyarylsulphones, cellulosics, regenerated cellulose, polyvinylidene fluoride and combinations thereof.

14. The method of claim 1, wherein in step (c) guanidine comprises guanidine hydrochloride.

15. The method of claim 1, wherein in step (c) guanidine comprises guanidine carbonate.

16. A method of removing unincorporated dye terminators from an unpurified DNA sequencing reaction product, comprising:
   a) providing at least one ultrafiltration membrane having at least one surface;
   b) providing a wash solution comprising EDTA and an amount of guanidine or salt thereof from about 0.5 to less than 5 mM effective for removing unincorporated dye terminators from the unpurified DNA sequencing reaction product;
   c) introducing the wash solution to the surface of the ultrafiltration membrane;
   d) providing the unpurified DNA sequencing reaction product having unincorporated dye terminators;
   e) introducing the unpurified DNA sequencing reaction product having the unincorporated dye terminators to the wash solution located on the surface of the ultrafiltration membrane; and
   f) applying a driving force to the ultrafiltration membrane to remove unincorporated dye terminators from the DNA sequencing reaction product, producing a purified DNA sequencing reaction product.

17. The method of claim 16, wherein in step (f) the driving force is maintained until the purified sequencing reaction product is filtered to dryness such that no visible fluid remains.

18. The method of claim 16, further comprising resuspending said purified DNA sequencing reaction product in a low ionic solution selected from the group consisting of water, formamide and mixtures thereof.

19. The method of claim 18, further comprising transferring said resuspended sequencing reaction product to a substrate for sequencing.

20. The method of claim 16, wherein in step (d) the ultrafiltration membrane has a molecular cutoff between about 1,000 and 30,000 Daltons.

21. The method of claim 16, wherein in step (c) guanidine comprises guanidine hydrochloride.

22. The method of claim 16, wherein in step (c) guanidine comprises guanidine carbonate.

23. A method of removing unincorporated dye terminators from an unpurified DNA sequencing reaction product, comprising:
   a) providing an unpurified DNA sequencing reaction product having unincorporated dye terminators;
   b) providing at least one ultrafiltration membrane having at least one surface;
   c) introducing the unpurified DNA sequencing reaction product having unincorporated dye terminators to the surface of the ultrafiltration membrane;
   d) providing a wash solution comprising EDTA and an amount of guanidine or salt thereof from about 0.5 mM to less than 5 mM effective for removing the unincorporated dye terminators from the unpurified DNA sequencing reaction product;
   e) introducing the wash solution to the unpurified DNA sequencing reaction product having unincorporated dye terminators located on the surface of the ultrafiltration membrane; and
   f) applying a driving force to the ultrafiltration membrane to remove the unincorporated dye terminators from the DNA sequencing reaction product, producing a purified DNA sequencing reaction product.

24. The method of claim 23, wherein in step (d) guanidine comprises guanidine hydrochloride.

25. The method of claim 23, wherein in step (c) the ultrafiltration membrane has a molecular cutoff between about 3,000 and 15,000 Daltons.

26. The method of claim 23, further comprising resuspending said purified sequencing reaction product in a low ionic solution, and transferring said resuspended sequencing reaction product to a substrate for sequencing.

27. The method of claim 23, wherein said solution comprising said amount of guanidine further comprises EDTA.

28. The method of claim 23, wherein in step (f) the driving force is maintained until the purified sequencing reaction product is filtered to dryness such that no visible fluid remains.

29. The method of claim 23, wherein in step (c) the ultrafiltration membrane comprises a well filter plate.

* * * * *